(12) United States Patent
Constantin et al.

(10) Patent No.: US 10,898,158 B2
(45) Date of Patent: Jan. 26, 2021

(54) PHANTOM SETUP AND SOURCE-TO-SURFACE DISTANCE VERIFICATION USING RADIATION IMAGING

(71) Applicant: Varian Medical Systems, Inc., Palo Alto, CA (US)

(72) Inventors: Magdalena Constantin, Los Altos, CA (US); HsinLu Hsu, Sunnyvale, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 255 days.

(21) Appl. No.: 16/300,923

(22) PCT Filed: May 11, 2017

(86) PCT No.: PCT/US2017/032120
§ 371 (c)(1),
(2) Date: Nov. 12, 2018

(87) PCT Pub. No.: WO2017/200834
PCT Pub. Date: Nov. 23, 2017

(65) Prior Publication Data
US 2020/0315567 A1    Oct. 8, 2020

Related U.S. Application Data

(60) Provisional application No. 62/338,902, filed on May 19, 2016, provisional application No. 62/338,275, filed on May 18, 2016.

(51) Int. Cl.
*A61B 6/00* (2006.01)
*A61N 5/10* (2006.01)

(52) U.S. Cl.
CPC .............. *A61B 6/583* (2013.01); *A61B 6/589* (2013.01); *A61N 5/1075* (2013.01); *A61B 6/4258* (2013.01)

(58) Field of Classification Search
None
See application file for complete search history.

(56) References Cited

U.S. PATENT DOCUMENTS

2005/0013406 A1*   1/2005   Dyk .................... A61N 5/1049
                                                                378/65
2007/0086561 A1   4/2007   Bruder
(Continued)

FOREIGN PATENT DOCUMENTS

EP          0218367 A1     4/1987

OTHER PUBLICATIONS

PCT, International Search Report and Written Opinion of International Searching Authority in PCT/US2017/032120, dated Jul. 14, 2017, 7 pages.

(Continued)

*Primary Examiner* — Edwin C Gunberg
(74) *Attorney, Agent, or Firm* — Varian IP Legal

(57) ABSTRACT

A phantom setup and source-to-surface distance (SSD) verification method uses radiation images. In an exemplary method, a phantom is positioned on a support relative to a radiation source such that a surface of the phantom is horizontally leveled at or approximate to a desired value of SSD. The radiation source is then positioned at a gantry angle predetermined at least based on the desired value of SSD such that a ray of radiation from the radiation source aligns with a horizontal surface located at the desired value of SSD. An image is acquired using radiation from the radiation source at the predetermined gantry angle. Verification is performed to confirm, based on an analysis of the (Continued)

image, if the surface of the phantom is positioned at the desired value of SSD.

20 Claims, 7 Drawing Sheets

(56) References Cited

U.S. PATENT DOCUMENTS

| | | |
|---|---|---|
| 2007/0253529 A1 | 11/2007 | Seppi |
| 2008/0064953 A1 | 3/2008 | Falco |
| 2008/0144913 A1 | 6/2008 | Yoshida |
| 2015/0352376 A1 | 12/2015 | Wiggers et al. |

OTHER PUBLICATIONS

European Patent Office, Supplementary European Search Report and Written Opinion in European Application No. 17 799 899.4, dated Nov. 21, 2019, 6 pages.

\* cited by examiner

PHANTOM SETUP AND SOURCE-TO-SURFACE DISTANCE VERIFICATION USING RADIATION IMAGING

TECHNICAL FIELD

Embodiments of this disclosure relate generally to radiation systems and methods. In particular, various embodiments of a method for phantom setup and verification of source-to-surface distance (SSD) using radiation imaging are described.

BACKGROUND

Radiation systems are used in a variety of applications including imaging and treatment of patients. To ensure safety and accurate dose delivery, various tests of radiation systems are performed on a daily, monthly, or yearly basis. For instance, acceptance tests are performed to assure that the specifications of a radiation machine manufactured meet the requirements of user agreements. Beam commissioning tests require measurements of radiation dose distributions in water (i.e. beam profiles and percent depth dose curves) among other measurements. Quality assurance (QA) tests are performed at regular time periods to assure that beams delivered by a radiation machine remain within the specifications and to test that the treatment planning system predictions for various treatment plans agree with the actual machine delivery for these plans.

In various tests of a radiation machine, phantoms are often used to simulate radiation transport through tissue or other materials which the radiation machine under test is used for. Phantom setup with precision is required for effective radiation beam tuning, dose calibration, beam commissioning, and so on. For example, knowing with precision source-to-surface distance (SSD), or the distance from the radiation source to the surface of a phantom, is important for dose calibration of a radiation machine. Conventionally, SSD is measured by using an optical distance indicator (ODI) installed in the collimation of a radiation machine. An ODI includes a light source and an optical lens assembly for focusing light from the light source to the phantom. The optical lens assembly includes a graduated lens having a plurality numbers etched or printed thereon for projecting a scale of numbers onto the phantom, indicating a distance from the source to the surface of the phantom. SSD is verified with a mechanical device that is typically attached to a precise mechanical surface of the radiation machine so that the distance from the source to the surface of the phantom can be measured physically with precision.

To integrate an ODI in a radiation machine increases the cost. To accommodate an ODI, cavities are provided in collimation and shielding components of the radiation machine, complicating the calculation and design of the shielding of the machine. Limited access to the ODI also complicates the maintenance and replacement of the components of the radiation machine. There are instances where a precise mechanical interface is not available for users to precisely verify the setup of a phantom with a mechanical device. Accordingly, there is a need for new methods to set up phantoms and verify SSD.

SUMMARY

Provided by this disclosure is a radiation system and method that allows phantom setup and verification of source-to-surface-distance (SSD) with sub-millimeter precision in a reliable, time-efficient way. The disclosed method allows accurate phantom setup when a precise mechanical surface in a radiation device is not available. The disclosed SSD verification method uses image acquisition, eliminates the need for additional tools and accessories as required in conventional SSD verification, and significantly reduces the time spent by an operator inside a vault or treatment room. According to embodiments of the disclosed method, SSD verification can be performed at a console located outside of a treatment room by acquiring e.g. a few MV-images with prescribed gantry rotations.

In an exemplary method, a phantom is positioned on a support relative to a radiation source such that a surface of the phantom is horizontally leveled at or approximate to a desired value of source-to-surface distance (SSD). The radiation source is then positioned at a gantry angle predetermined at least based on the desired value of SSD such that a ray of radiation from the radiation source aligns with a horizontal surface located at the desired value of SSD. An image is acquired using radiation from the radiation source at the predetermined gantry angle. Verification is performed to confirm, based on an analysis of the image, if the surface of the phantom is positioned at the desired value of SSD.

In another exemplary method, a phantom is positioned on a support relative to a radiation source such that a surface of the phantom is horizontally leveled at or approximate to a desired SSD value of 100 centimeter. The radiation source is supported by a gantry rotatable about an isocenter distanced from the radiation source at 100 centimeter. The gantry is rotated about the isocenter to position the radiation source at a gantry angle of 90 or 270 degree. An image is acquired using radiation from the radiation source at the gantry angle of 90 or 270 degree. Verification is performed to confirm, based on an analysis of the image, if the surface of the phantom is positioned at the desired SSD value of 100 centimeter.

In an exemplary method, an object such as a phantom is set up to a desired location using an imager panel. When a surface of the object is aligned with a radiation source, the penumbra is minimum. Penumbra refers to the region at the edges of a radiation beam over which a rapid change in dosage rate or intensity occurs, resulting in a blurred region on an image. Therefore, according to the exemplary method, the surface of the object is aligned with the radiation source such that the penumbra is minimum, resulting in a geometric sharpness on the image.

The surface of the object can be flat or curve or in other shapes. In embodiments where the surface of the object is flat such as a water phantom surface, the flat surface can be aligned to be co-planar with the radiation source. In embodiments where the surface of the object is curved such as a cylindric phantom surface, the tangent of the curve surface can be aligned with the radiation source. In principle, the surface of the object is aligned with the source such that the material in which the radiation beam goes through has the most rapid change that results in the sharpness of the penumbra.

The penumbra sharpness can be distinguished by human eyes or computer software. The sharpness resulting from a large water phantom surface can be generally distinguished by human eyes due to the rapid change in the material that the radiation beam goes through.

The exemplary method can be implemented in either isocentric or non-isocentric devices. In a non-isocentric device, a radiation source is typically positioned at a known location relative to a known reference point such as the in-room isocenter or a reference point. In such system, the radiation source can be at any distance or any angle relative to the object under irradiation. To position an object such as a water phantom, the water surface can be aligned with the radiation source using images acquired with radiation from the radiation source. The imaging panel can be integrated in the device e.g. capable of moving in synchronization with the radiation source. Alternatively, the imaging panel can be an independent device. The imaging panel location may be known relative to the reference point although that is not required. In either situation, the location of the object such as a water phantom surface can be determined by where the minimum of the penumbra occurs, identified either by human eyes or by computer software on the acquired images.

To verify the intended location of the object using the same panel described above, the imaging panel location and the position and angle relative to the reference point can be used, following the examples and illustrations as will be described below for an isocentric on-board imager device.

This Summary is provided to introduce selected embodiments in a simplified form and is not intended to identify key features or essential characteristics of the claimed subject matter, nor is it intended to be used as an aid in determining the scope of the claimed subject matter. The selected embodiments are presented merely to provide the reader with a brief summary of certain forms the invention might take and are not intended to limit the scope of the invention. Other aspects and embodiments of the disclosure are described in the section of Detailed Description.

BRIEF DESCRIPTION OF THE DRAWINGS

These and various other features and advantages will become better understood upon reading of the following detailed description in conjunction with the accompanying drawings and the appended claims provided below, where:

DETAILED DESCRIPTION

Figure 1:
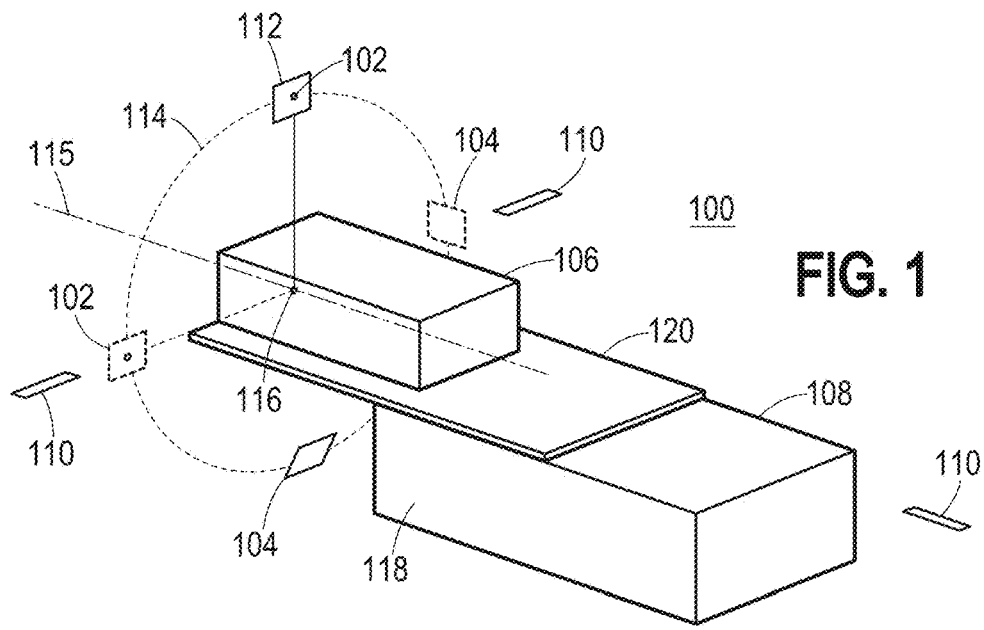
FIG. 1 illustrates a radiation system that can implement various embodiments of a method of the disclosure.

Various embodiments of a method and system for phantom setup and source-to-surface distance (SSD) verification are described. It is to be understood that the disclosure is not limited to the particular embodiments described. An aspect described in conjunction with a particular embodiment is not necessarily limited to that embodiment and can be practiced in any other embodiments.

Various embodiments are described with reference to the figures. It should be noted that some figures are not necessarily drawn to scale. The figures are only intended to facilitate the description of specific embodiments, and are not intended as an exhaustive description or as a limitation on the scope of the disclosure. Further, in the figures and description, specific details may be set forth in order to provide a thorough understanding of the disclosure. It will be apparent to one of ordinary skill in the art that some of these specific details may not be employed to practice embodiments of the disclosure. In other instances, well known components may not be shown or described in detail in order to avoid unnecessarily obscuring embodiments of the disclosure.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. The term "first" or "second" etc. may be used to distinguish one element from another. The use of the term "first" or "second" should not be construed as in any particular order unless the context clearly dictates otherwise. Further, a method may be described in a series of steps specified in the flowchart or the claims. It should be noted that it is not necessary to carry out the series of steps in a particular order in conducting the method unless the context clearly dictates otherwise.

As used herein, the term "radiation source" refers to a source operable to generate radiation including but not limited to x-rays, gamma-rays, protons, heavy ions, and electrons, etc. By way of example, a radiation source may include a target or metallic component which produces radiation of x-rays upon impingement of electrons from an electron accelerator. The radiation source may be a source operable to produce radiation suitable for either treatment or imaging or both.

As used herein, the term "gantry" refers to a structure configured to carry or support a radiation source. The term "gantry angle" refers to an angular position of a radiation source supported by a gantry relative to a vertical axis as viewed from a horizontal axis about which the gantry supporting the radiation source can rotate. In the following description and claims, gantry angles or axes of specific degrees may be set forth in describing various embodiments. It should be noted that reference to a specific degree of a gantry angle or an axis includes degrees within plus or minus 0.1 degree from the stated specific degree.

As used herein, the term "source-to-surface distance" (SSD) refers to the distance from a radiation source at a gantry angle to a point on a surface of an object such as a phantom. The term "source-to-isocenter distance" (SID) refers to the distance from a radiation source to an isocenter. In the following description and claims, SSD or SID of a specific value may be set forth in describing various embodiments. It should be noted that reference to a specific value of SSD or SID includes distances within plus or minus 0.1 millimeter from the stated specific distance.

As used herein, the term "phantom" refers to an object that simulates radiation attenuation through a tissue-equivalent, bone-equivalent, muscle-equivalent, metallic or other materials which a radiation machine under test is used for. A phantom receives radiation dose during evaluation of a radiation machine in acceptance tests, beam commissioning, beam tuning, dose calibration, and various quality assurance tasks. A phantom includes but is not limited to water tank phantom used for beam commissioning, water-equivalent solid blocks with rectangular shapes, phantoms with human-like shapes (anthropomorphic) which can also have various materials to simulate the tissue, muscles, bones and metal implants, and any other suitable quality assurance (QA) devices. A phantom may be in a shape of a cubold, cube, cylinder, sphere, prism, or polyhedron, or any other regular or irregular shapes. A phantom may comprise a flat surface or a curve surface or a combination of flat and curve surfaces.

Disclosed herein is a novel method for phantom setup and SSD verification using radiation image acquisition with prescribed gantry rotations. For radiation apparatus equipped with on-board imagers, the disclosed method takes advantage of the machine being an image-guided radiotherapy system.

FIG. 1 depicts an exemplary radiation system 100 in which embodiments of a method according to this disclosure can be implemented. The radiation system 100 may be a treatment system, an imaging system, a simulation system, a research and developmental system, or any other suitable radiation system. In a general configuration, the radiation system 100 includes a radiation source 102 and an imager 104. An object 106, such as a patient or phantom, may be placed on a support 108. Two or more lasers 110 may be provided to facilitate setup of the object 106 relative to the radiation source 102 and/or isocenter 116.

The radiation source 102 may be any suitable source operable to generate radiation, including but not limited to, x-rays, gamma-rays, protons, heavy ions, and electrons, etc. By way of example, the radiation source 102 may include a target or metallic component which produces radiation of x-rays upon impingement of electrons from an electron accelerator. Radiation produced by the radiation source 102 may be suitable for either treatment or imaging, or may have an energy level at megavolts (MV) or kilovolts (KV). While not shown, the radiation system 100 may include a collimator configured to define the size, shape, or angle of the radiation generated by the source 102. For example, a collimator may have a collimation angle ranging e.g. from 5 to 20 degrees.

The radiation source 102 may be supported by a gantry 112. The gantry 112 may rotate, as indicated by the dashed line 114, about an axis 115 passing through the isocenter 116 in positioning the radiation source 102 at a gantry angle. The gantry 112 may be in the shape of a C-arm on which the radiation source 102 can be mounted in a cantilevered manner. The gantry 112 may also be in the shape of a toroid or ring having an opening to allow at least a portion of the object 106 to extend through. In some embodiments, the gantry 112 supporting the radiation source 102 may ride or rotate on a ring structure. The ring structure can be a complete or partial ring structure providing a circular or arc rotating orbit. In alternative embodiments, the gantry 112 may be in the form of a robotic arm that has multiple motion degrees of freedom. For example, an articulated robotic arm may have four, five or six rotational degrees of freedom. The radiation source 102 mounted on an articulated robotic arm can be positioned at one of a plurality of known locations or nodes, which can be at any distance or angle relative to the object 106 and/or an in-room reference point. Such system may be referred to as a non-isocentric system.

The imager 104 may be operably disposed opposite to the radiation source 102. The imager 104 may be mounted on the gantry 112 or rotated in synchronization with the source 102. Alternatively, the imager 104 is not mounted on the gantry 112 or an independent device. In some embodiments, the imager 104 may be an electronic portal imaging device (EPID) configured to acquire images with radiation having an energy level at megavolts (MV). Alternatively, the imager 104 may be configured to acquire images with radiation having an energy level at kilovolts (kV).

The imager 104 may be a flat panel imager known in the art.

Two or more lasers 110 may be provided to facilitate patient or phantom setup. The two or more lasers 110 may be disposed on the side walls and/or ceiling of the room where the radiation system 100 is located. In embodiments of a ring gantry, the lasers 110 may also be disposed on an outer cover enclosing the rotating source and imager. The two or more lasers 110 may be mounted such that light from the lasers 110 may intersect at the isocenter 116.

The support 108 may include a patient couch 118 and a platform 120 which can move in multiple degrees of freedom. For example, the couch 118 may move vertically thereby allowing the object 106 to be moved up and down. The platform 120 may move horizontally thereby allowing the object 106 to be moved longitudinally and/or laterally in positioning. The platform 120 may rotate, e.g. yaw, pitch and roll in positioning the object 106 relative to the radiation source 102. The couch 118 may also rotate on the ground via a base member (not shown). In alternative embodiments, the support 108 may be a structure constructed or configured to support a phantom or QA device for various tests or QA tasks. The movement of the support 108 can be controlled via a console (not shown) located remotely from the support 108. As used herein, the term "remotely located" or its grammatical equivalent refers to being located in a place separate from the room where the support or source is located. By way of example, a console may be remotely located in a control room which is separated or shielded from a treatment room, an imaging room, or a simulation room where the support 118 is located.

The object 106 may be a patient, a phantom, or any suitable devices for various quality assurance (QA) tasks. By way of example, the object 106 may be a water phantom including a tank for holding water and corresponding scanning system. The level of water can be adjusted by increasing or decreasing the amount of water in the tank. The water phantom may include a probe or radiation detector and a mechanism e.g. horizontally and/or vertically moving the probe in the water. By measuring radiation dose with the probe at different locations in the water phantom, features or profiles of radiation beams can be characterized. The object 106 may be a solid water phantom including a plurality of blocks which can be individually added or removed in adjusting the horizontal level of the phantom. The object 106 may also be other types of phantoms or QA devices incorporating a radiation detector providing measured data representative of the features of beams from the radiation source 102.

As discussed above, phantom setup with precision is desirable for effective radiation beam tuning, dose calibration, and beam commissioning. For example, knowing with precision source-to-surface distance (SSD) is important for dose calibration of the radiation apparatus. Embodiments of the disclosure provide a radiation image-based method to facilitate phantom setup and verify SSD with sub-millimeter precision.

Figure 2:
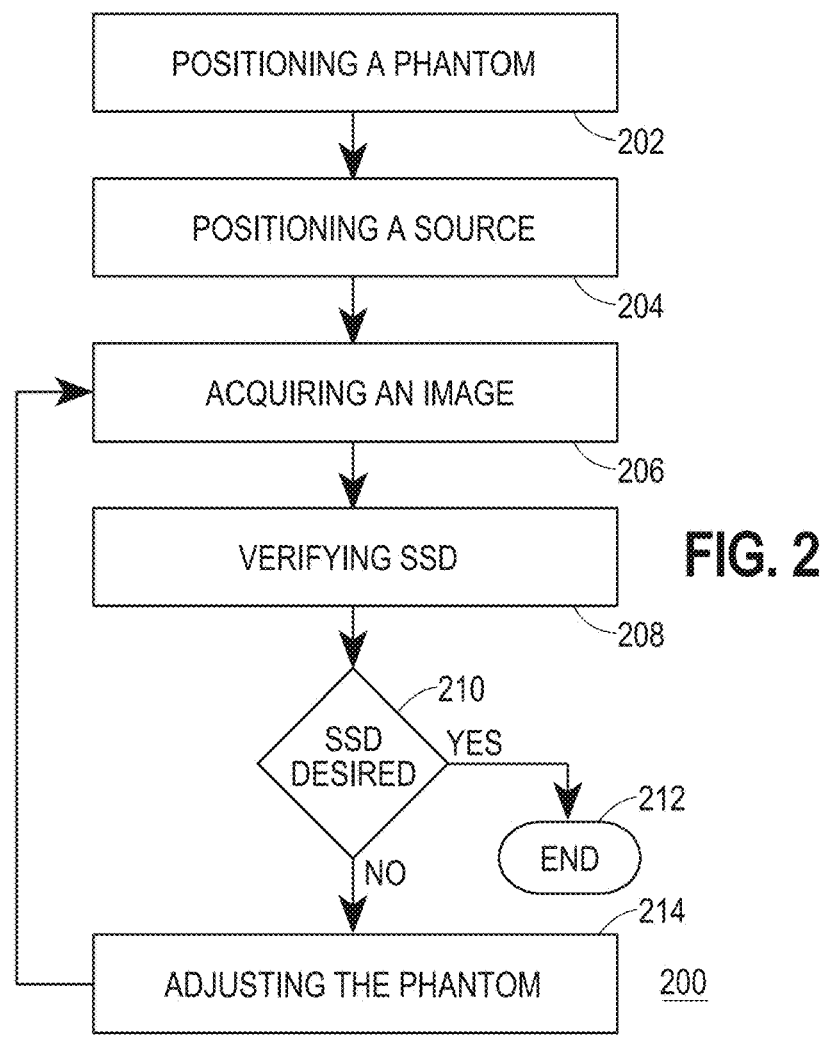
FIG. 2 is a flowchart showing an exemplary method for phantom setup and SSD verification according to embodiments of this disclosure.

FIG. 2 is a flowchart illustrating an exemplary method 200 for phantom setup and SSD verification according to embodiments of the disclosure. While the method 200 will be described with reference to the exemplary system 100 shown in FIG. 1, the method 200 can be implemented in any other suitable isocentric or non-isocentric system.

The method 200 may start by positioning a phantom 106 on a support 108 (step 202). The support 108 may be a patient support configured for treatment and imaging described above in conjunction with FIG. 1. Alternatively, the support 108 may be a structure constructed to support a phantom or QA device for various tests of a radiation apparatus.

The phantom 106 may be positioned on the support 108 such that the surface of the phantom is horizontally leveled. In various embodiments of the disclosure, the phantom 106 comprises a water phantom, and its surface can be horizontally leveled by virtue of its fluidity. Other types of phantoms or QA devices may be horizontally leveled by e.g. adjusting the support 108 and/or using lasers 110 etc.

The horizontal surface of the phantom 106 may be initially positioned at least approximate to a desired SSD. For example, the phantom 106 may be moved or adjusted such that the horizontal surface of the phantom is located approximately at 100, or 95, or 90 centimeter SSD as commonly used for various QA tests or clinical applications. The position of the phantom 106 may be adjusted by moving the support 108 vertically e.g. from a console remotely located or by changing the amount of the phantom. For example, the surface level of a water phantom may be adjusted by increasing or decreasing the amount of water in a water tank. The surface level of a solid water phantom may be adjusted by adding or removing individual phantom blocks. Alternatively, the support 108 may be moved vertically to adjust the level of the horizontal surface of the phantom 108. Any suitable means or combination thereof may be used to bring the horizontal surface of the phantom 106 close to a desired SSD position.

The initial positioning of the phantom surface may be facilitated by the use of lasers 110. For example, a tank of a water phantom may be illuminated by lasers 110 with lines indicating desired position levels e.g. 100 centimeter SSD. While the laser lines may not precisely reflect the SSD position because the lasers may be mounted to a mechanical structure that is not an accurate interface with the radiation source, adding water e.g. to a level close to a desired SSD position e.g. smaller than 100 centimeter SSD with the help of lasers may reduce the extent of movement of the support in subsequent verification and adjustment, which may be advantageous in avoiding collision in situations where the clearance between the radiation source and the phantom is limited.

Referring to FIG. 2, at step 204, the radiation source 102 is positioned at a gantry angle that correlates to the desired SSD. In general, the radiation source 102 is positioned at a gantry angle predetermined such that a ray of radiation from the radiation source 102 is tangent to or aligns with a horizontal surface that is located at a desired SSD.

Figure 3:
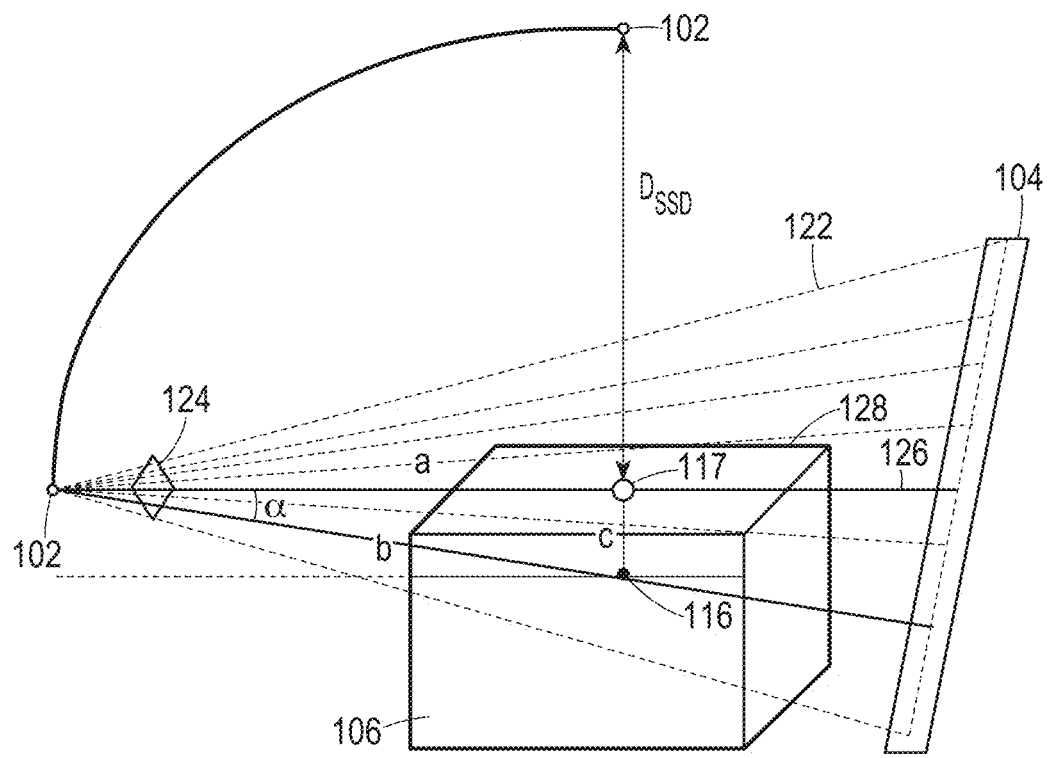
FIG. 3 schematically shows a phantom setup for SSD verification according to embodiments of this disclosure.

FIG. 3 schematically shows the positioning of a radiation source 102. The radiation source 102 may be rotated by a gantry. By way of example, a gantry may rotate the radiation source 102 about the isocenter 116, e.g. from a gantry angle of zero degree to a gantry angle of non-zero degree as shown. The imager 104, which may be rotated in synchronization with the source 102, is operably positioned opposite to the radiation source 102. Radiation 122 from the source 102, collimated by a collimator 124 and passing through the phantom 106 and a surrounding medium such as air or other gaseous media, deposits on the imager 104 forming an image. At a predetermined gantry angle, which can be calculated as will be described in greater detail below, a ray 126 of radiation 122 may be tangent to or align with a horizontal surface located at a desired SSD value. In FIG. 3, the horizontal surface of the phantom 106 is indicated at 128. A probe or dose detector is indicated at 117. If the horizontal surface 128 of the phantom 106 is setup precisely at the desired SSD, the ray 126 of radiation will be tangent to or align with the horizontal surface 128 of the phantom 106 and deposit on the imager 104, forming an image showing a clear crisp interface between the phantom 106 and the surrounding medium. When the tangency configuration happens, the penumbra of the radiation passing through the surrounding medium-phantom interface is minimal, therefore the resulting interface image is crisp. On the other hand, if the horizontal surface 128 of the phantom 106 is setup off the desired SSD, radiation rays from the source 102 at the gantry angle will not be tangent to or align with the horizontal surface 128 of the phantom 106. As a result, the portion of the image formed on the imager 104 showing the interface between the phantom 106 and the surrounding medium will be blurry due to the scattering effect of radiation passing through the interface between the phantom and surrounding medium. When the tangency configuration does not happen, the penumbra of the radiation passing through the surrounding medium-phantom interface is large due to scattering, therefore the resulting interface image is blurred.

The gantry angle can be predefined according to the principle of trigonometry. As shown in FIG. 3, in the triangle defined by source 102, angle ($\alpha$), sides a, b, and c, where side a is on the horizontal surface located at the desired SSD, side b passes through the isocenter 116, and side c is perpendicular to side a, the relationship can be defined as $\sin(\alpha)=c/b$. For description of embodiments, $D_{SSD}$ is used herein to represent the desired SSD value, and $D_{ISO}$ is used to represent the distance between the isocenter 116 and the radiation source 102. Thus, the relationship can also be expressed as $\sin(\alpha)=(D_{ISO}-D_{SSD})/D_{ISO}$ or alpha ($\alpha$)=arcsin$(D_{ISO}-D_{SSD})/D_{ISO}$.

Therefore, the gantry angle can be predefined according to the following equation:

$$90-\arcsin(D_{ISO}-D_{SSD})/D_{ISO} \qquad (I)$$

or $$270+\arcsin(D_{ISO}-D_{SSD})/D_{ISO} \qquad (II)$$

Equations (I) and (II) can be used to calculate or predefine the gantry angle of the radiation source 102 for verification of any desired SSD according to the disclosed method.

Figure 4:
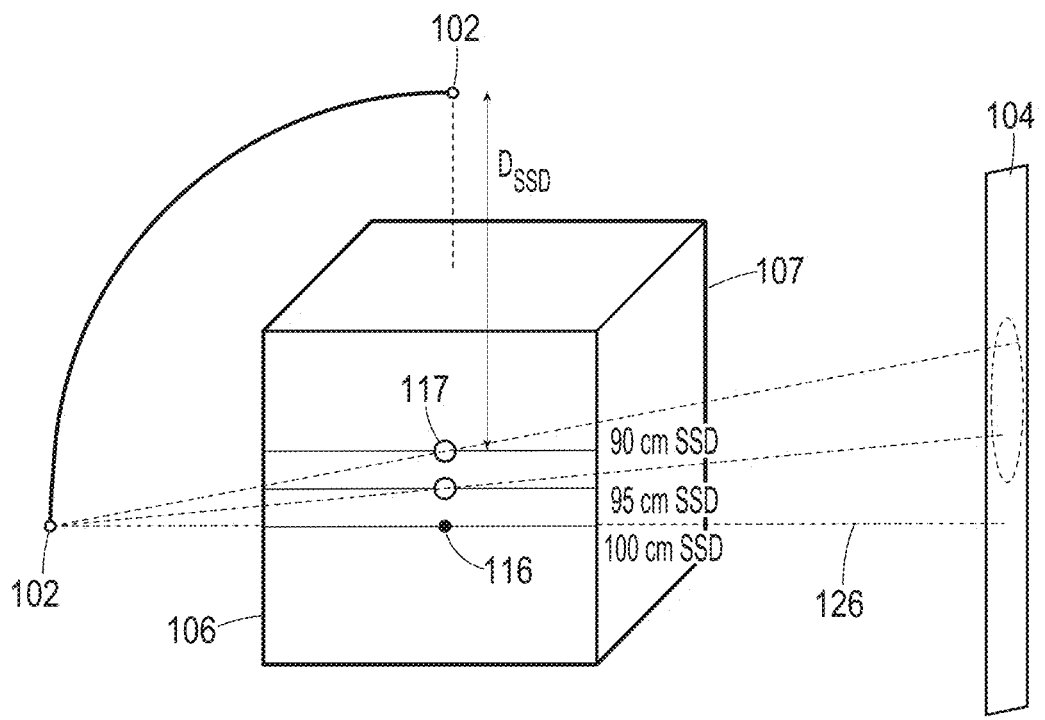
FIG. 4 schematically shows a radiation source positioned at a predetermined gantry angle of non-zero degree for SSD verification of a phantom setup according to a specific embodiment of this disclosure.

FIG. 4 schematically shows a specific example for determining the gantry angle of a radiation source for verification of a phantom setup at 100 centimeter SSD. In the example shown in FIG. 4, the phantom 106 includes water held in a tank 107 and a probe or radiation detector 117. In a radiation system with an isocenter 116 distanced at 100 centimeter from the source 102, if the desired SSD for phantom setup is 100 centimeter, the gantry angle will be 90 degree or 270 degree as calculated according to the above Equations (I) or (II). In other words, the positioning of the source 102 at the gantry angle of 90 degree or 270 degree will allow the source 102 to vertically align with a horizontal surface located at a desired SSD value of 100 centimeter, or allow a ray of radiation 126 from the source 102 to be tangent to or align with a horizontal surface located at the desired 100 centimeter SSD. If the phantom or water surface is actually or precisely set up at 100 centimeter SSD, a ray of radiation 126 from the source 102 will be tangent to or align with the phantom surface and deposit on the imager 104, forming an image showing a clear crisp interface between the phantom 106 and the surrounding medium, as will be shown in greater detail below.

FIG. 4 further shows that if the phantom surface is set up off the desired 100 centimeter SSD, e.g. at 95 or 90 centimeter SSD, then radiation from the source 102 positioned at the gantry angle of 90 or 270 degree as predefined for verification of phantom setup at 100 centimeter SSD does not provide any ray of radiation tangent to or aligned with a horizontal surface located at 95 or 90 centimeter SSD. Images acquired with radiation from the source positioned at the gantry angle of 90 or 270 degree will show a blurry phantom-surrounding medium interface, as will be shown in greater detail below.

Figure 5:
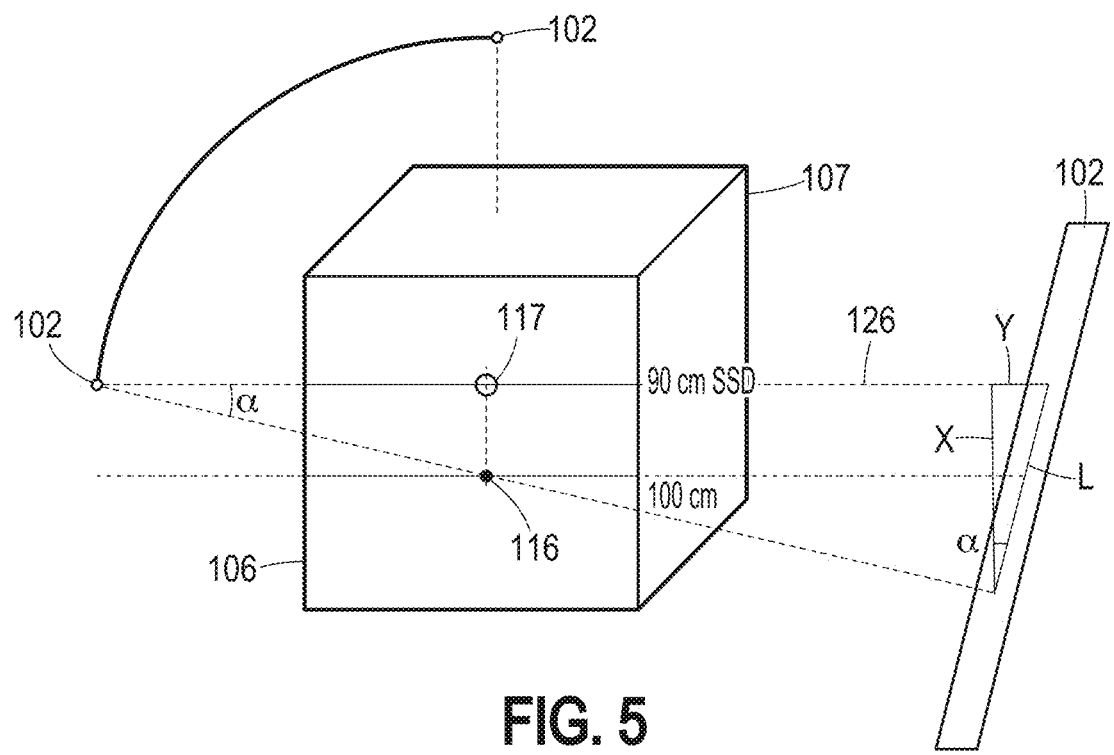
FIG. 5 schematically shows a radiation source positioned at a predetermined gantry angle of non-zero degree for SSD verification of a phantom setup according to another specific embodiment of this disclosure.

FIG. 5 schematically shows another specific example for determining the gantry angle of the radiation source for verification of a phantom setup at 90 centimeter SSD using the method of the present disclosure. According to Equations (I) and (II), for a desired SSD value of 90 centimeter, the positioning of the radiation source at a gantry angle of 84.3 or 275.7 degree will provide a radiation beam with a ray being tangent to or aligned with a horizontal surface located at 90 centimeter SSD. Therefore, if a phantom surface is actually set up at the desired 90 centimeter SSD, radiation from the source 102 positioned at a gantry angle of 84.3 or 275.7 degree would produce an image showing a noiseless or scatter-free phantom-surrounding medium interface characterized by a sharp contrast, as will be shown in greater detail below.

FIG. 5 further shows that the location of the phantom-surrounding medium interface will be shifted (L) from the projected isocenter line on the acquired image. As shown, in a triangle defined by angle alpha (α), sides x, y, and L, the relationship can be expressed as $\cos(\alpha)=x/L$ or $\cos(\alpha)=(D_{ISO}-D_{SSD})/L$. Therefore, the shift (L) of the phantom-surrounding medium interface from the projected isocenter line on the acquired image can be determined according to the following Equation (III):

$$L=(D_{ISO}-D_{SSD})/\text{Square root of } \{1-[(D_{ISO}-D_{SSD})/D_{ISO}]^2\} \quad (III)$$

In the specific example shown in FIG. 5, the shift of the phantom-surrounding medium interface (L) from the projected isocenter line on the acquired image is 10.0504 centimeter as calculated according to Equation (III).

Figure 6:
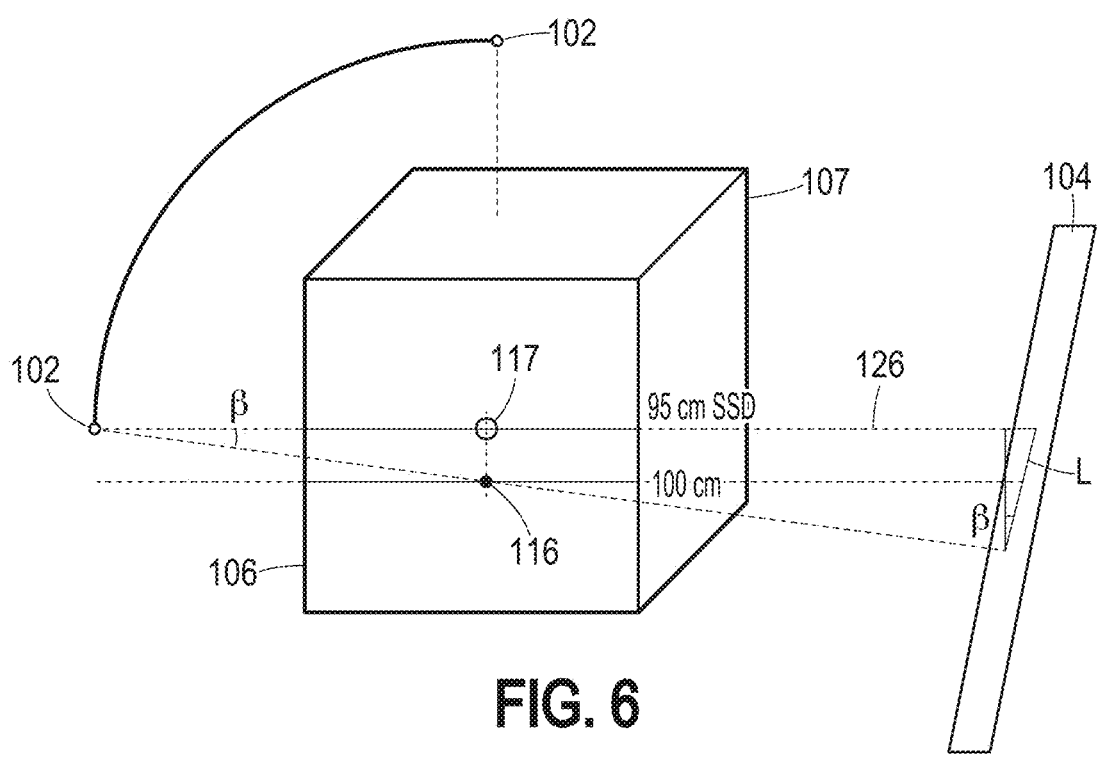
FIG. 6 schematically shows a radiation source positioned at a predetermined gantry angle of non-zero degree for SSD verification of a phantom setup according to a further embodiment of this disclosure.

FIG. 6 schematically shows another specific example for determining the gantry angle of the radiation source for verification of a phantom setup at 95 centimeter SSD using the method of the present disclosure. According to Equations (I) and (II), for verification of a phantom surface at a desired SSD value of 95 centimeter, the positioning of the source 102 at a gantry angle of 87.1 or 272.9 degree will provide radiation with a ray of radiation being tangent to or aligned with a horizontal surface located at 95 centimeter SSD. Therefore, if a phantom surface is actually set up at the desired 95 centimeter SSD, radiation from the source 102 positioned at a gantry angle of 87.1 or 272.9 degree would produce an image showing a noiseless or scatter-free phantom-surrounding medium interface characterized by a sharp contrast, as will be shown below.

Further, in the specific example shown in FIG. 6, the location shift of the phantom-surrounding medium interface (L) from the projected isocenter line on the acquired image is 5.0063 centimeter as calculated according to Equation (III).

Returning to FIG. 2, at step 206 an image showing the phantom-surrounding medium interface is acquired. The image can be obtained by an imager such as a flat panel imager known in the art. In some embodiments, the imager may be an electronic portal imaging device (EPID) equipped in a treatment system. Therefore, an image may be acquired using radiation having an energy level at megavolts from a therapeutic radiation source. In alternative embodiments, an image may be acquired with radiation having an energy level at kilovolts from an imaging source.

At step 208, verification is performed to determine if the phantom surface is set up at the desired SSD. According to embodiments of the disclosure, the verification can be based on an analysis of the acquired image showing the phantom-surrounding medium interface. For example, the analysis may include viewing or analyzing the contrast of the image showing the phantom-surrounding medium interface, either by human eyes or computer software. The analysis may include determining if the phantom-surrounding medium interface on the image is blurry, an indication that the phantom surface is not set at the correct SSD with precision, or if the phantom-surrounding medium interface on the image is sharp or clear, an indication that the phantom surface is precisely set at the desired SSD. The analysis may also include measuring the shift of location of the phantom-surrounding medium interface from the isocenter line of the graticule on the acquired image. Advantageously, the verification is imaged-based, eliminating the need for a field light, an optical distance indicator, or any mechanical tools required by conventional verification methods. The verification can be performed at a console located outside of a treatment room, significantly reducing the time spent by an operator inside a vault or treatment room.

Figure 7:
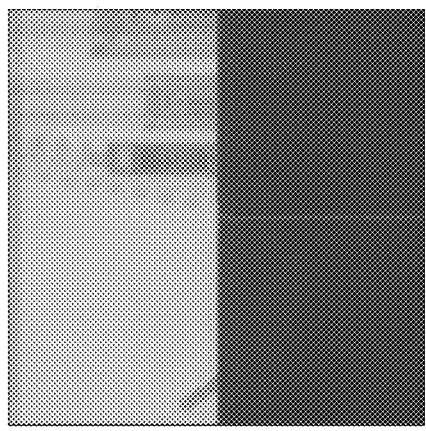
FIG. 7 shows images acquired with radiation from a radiation source positioned at a gantry angle for a phantom located at various SSDs according to embodiments of the disclosure.
Figure 7:
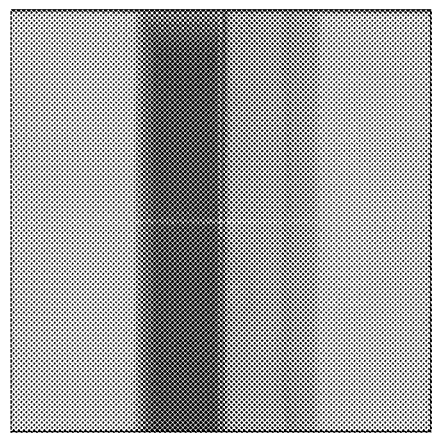
Figure 7:
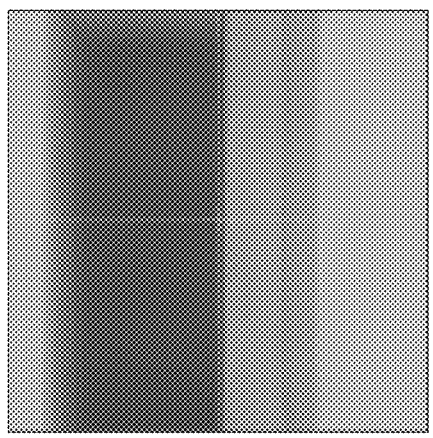

FIG. 7 shows three images of a solid water phantom acquired with radiation from a source at a gantry angle of 90 degree. The images were acquired from the solid water phantom set at different SSDs. The image on the top shows a clear and crisp phantom-air interface at the iso-plane, indicating that the phantom surface was set precisely at the desired 100 centimeter SSD. In comparison, the image in the middle, acquired as the phantom surface was set at 95 centimeter SSD, shows a blurry phantom-air interface, shifting to the left from the iso-plane. The image at the bottom, acquired as the phantom surface was set at 90 centimeter SSD, also shows a blurry phantom-air interface shifting further to the left from the iso-plane.

Figure 8:
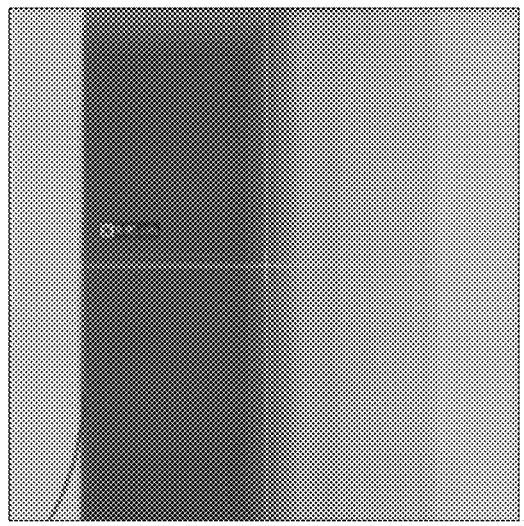
FIG. 8 shows images acquired with radiation from a radiation source positioned at various gantry angles for a phantom located at a particular SSD according to embodiments of the disclosure.
Figure 8:
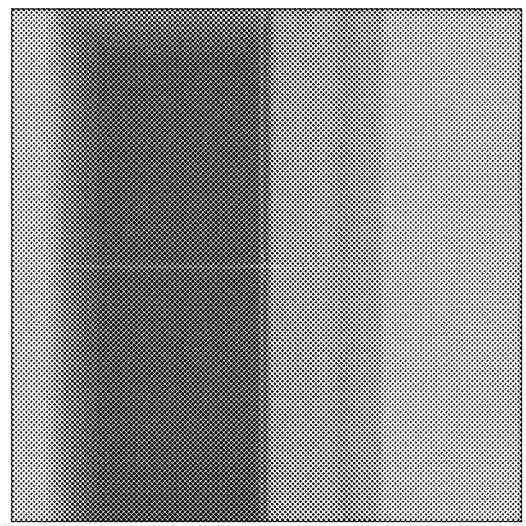

FIG. 8 shows two images of a solid water phantom set at 90 centimeter SSD. The images were acquired with radiation from a radiation source positioned at different gantry angles. The image at the bottom, acquired with radiation from the source at a gantry angle of 90 degree, shows a blurry phantom-air interface shifting to the left from the iso-plane. The image on the top, acquired with radiation from the source at a gantry angle of 84.3 degree predefined according to Equation (I) based on the desired SSD value of 90 centimeter, shows a clear crisp phantom-air interface shifting to the left from the isocenter plane as expected.

Figure 9:
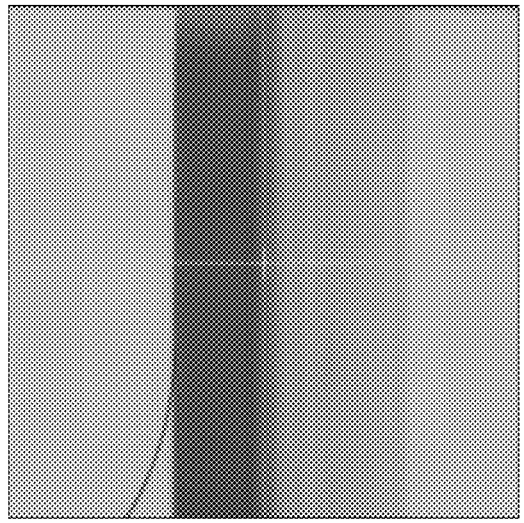
FIG. 9 shows images acquired with radiation from a radiation source positioned at various gantry angles for a phantom located at another particular SSD according to embodiments of the disclosure.
Figure 9:
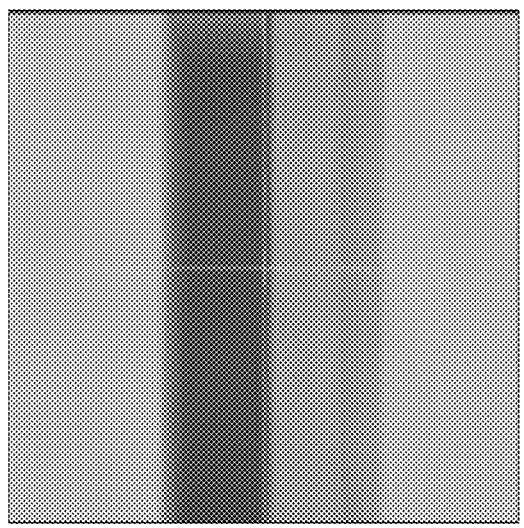

FIG. 9 shows two images of a solid water phantom set at 95 centimeter SSD. The images were acquired with radiation from a radiation source positioned at different gantry angles. The image at the bottom, acquired with radiation from the source at a gantry angle of 90 degree, shows a blurry phantom-air interface shifting to the left from the isocenter plane. The image on the top, acquired with radiation from the source at a gantry angle of 87.1 degree predefined according to Equation (I) based on the desired SSD value of 95 centimeter, shows a clear crisp phantom-air interface shifting to the left from the isocenter plane as expected.

Returning to FIG. 2 at step 210, if the verification confirms that the phantom 106 is correctly set up at the desired SSD, the process may end at 212. If the verification confirms that the phantom 106 is set up at a position deviating from the desired SSD, then the process may proceed to step 214, to further adjust a position of the phantom 106 in order to bring the phantom to the desired SSD. The position of the phantom 106 may be adjusted by moving the support 108 and/or by increasing or decreasing the amount of the phantom 106 as described above. The process may then proceed to step 206, repeating the steps of acquiring an image of the phantom, verifying SSD based on an analysis of the acquired image, until the verification confirms that the phantom is set up at the desired SSD with precision. As used herein, the term "precision" in the context of phantom setup and SSD verification according to embodiments of the disclosure refers to a sub-millimeter scale. As an example, 0.1 degree error in the gantry rotation translates into 0.1 millimeter error for the phantom surface position which can be identified on the acquired images using the methodology described in this disclosure.

Embodiments of a method for verifying source-to-surface distance of an object have been described. The disclosed method uses image acquisition with prescribed gantry rotations to identify the surrounding medium-phantom interface on the acquired images and confirms that the interface is at the expected distance from the isocenter plane. The image-based SSD verification method is fast, human-error free, and does not require any additional measuring tools or accessories. It can be applied in an iterative loop if images are desired with small couch shift (e.g. less than 1 millimeter) to double check the SSD alignment. The procedure for verifying SSD using image acquisition according to this disclosure can be an extremely fast. For example, an MV image only requires delivery of 1 to 2 machine units (MU). With a dose delivery rate of about 45 MU/min, the SSD verification task can be completed in no more than 3 seconds.

The image-based SSD verification can be performed using an on-board imaging system, leading to considerable cost saving by eliminating an optical distance indicator (ODI) or field lights from the radiation apparatus, hence allowing an optimization of the shielding components that have cavities and complex shapes in order to accommodate the field lights and ODI as in traditional radiation systems. For example, by eliminating the mirror needed for the light field in a radiation system, radiation shielding can be drastically improved close to the beam aperture. In addition, no specific tools or accessories will be needed to the verify SSD, as an imager is already integrated with the radiation machine in modern image-guided radiotherapy systems and the image acquisition can be fully enabled by a control system.

Figure 10:
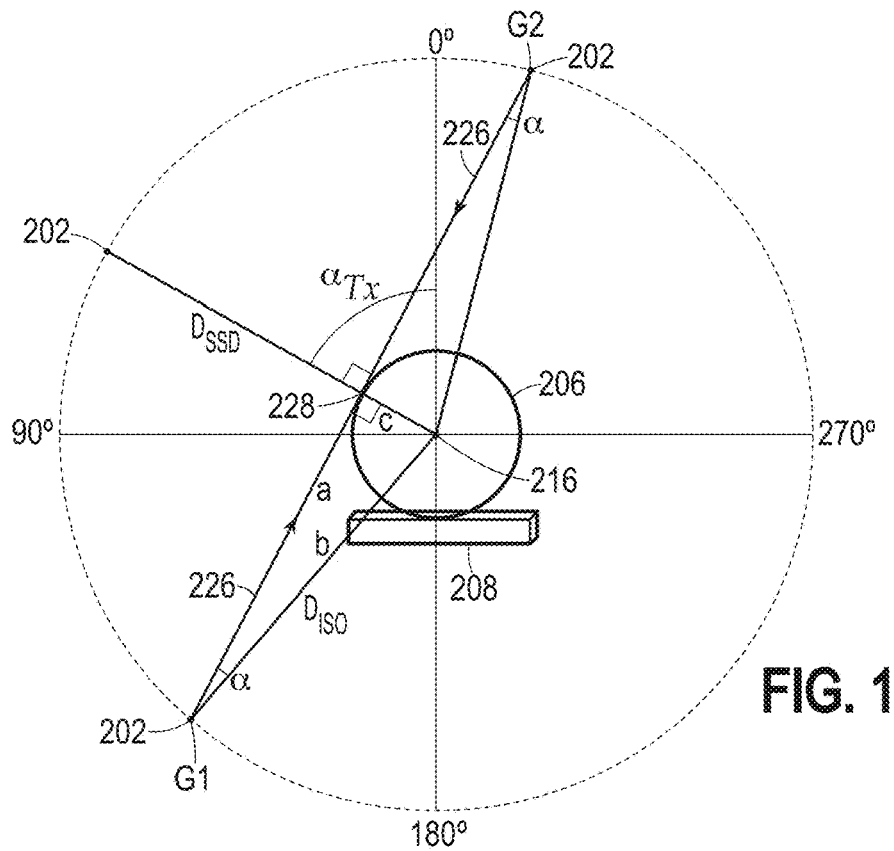
FIG. 10 schematically shows a phantom setup and SSD verification according to alternative embodiments of the disclosure.

FIG. 10 schematically shows a phantom setup and SSD verification according to an alternative embodiment of the disclosure. In FIG. 10, a phantom 206 supported by a support 208 is shown to be in a cylindrical shape having a curve surface. A radiation source 202 positioned at a first gantry angle ($\alpha_{Tx}$) defines a source-to-surface distance ($D_{SSD}$) from the source 202 to a point 228 on the curve surface of the phantom 206. The first gantry angle may be an angle for treatment or an angle for various QA measurements. The first gantry angle can be any angle known. According to the disclosure, radiation imaging can be used to set up the phantom 206 and verify if the phantom 206 is positioned at a desired value of SSD.

According to embodiments of the disclosure, the radiation source 202 can be positioned at a predetermined second gantry angle, indicated at G1 or G2, such that a ray of radiation 226 from the source 202 is tangent to an imaginary point on an imaginary curve surface located at a desired value of SSD. If the phantom 206 is setup correctly at the desired value of SSD, the ray of radiation 226 from the source 202 at the second gantry angle G1 or G2 is tangent to the point 228 on the curve surface of the phantom 206, forming an image showing a sharp or crisp interface between the phantom 206 and the surrounding medium because the resulting penumbra is minimal. On the other hand, if the phantom 206 is not set up at the correct SSD, the ray of radiation 226 from the source 206 at the second gantry angle will not be tangent to the point 228 on the curve surface of the phantom 206. As a result, the portion of the image formed showing the interface of the phantom 206 and the surrounding medium will be blurry due to the large penumbra caused by the scattering effect of radiation passing through the interface.

The second gantry angle of the radiation source 202 at G1 or G2 can be predetermined according to the principle of trigonometry. As shown in FIG. 10, in the triangle defined by source 202 at G1, angle ($\alpha$), sides a, b, and c, where side a is tangent to the imaginary point, side b passes through the isocenter 216, and side c is perpendicular to side a, the relationship can be defined as $\sin(\alpha)=c/b$, or $\sin(\alpha)=(D_{ISO}-D_{SSD})/D_{ISO}$ wherein $D_{SSD}$ represents a desired value of SSD and $D_{ISO}$ represents the distance between the isocenter 216 and the radiation source 202. Thus, the relationship can also be expressed as alpha $(\alpha)=\arcsin(D_{ISO}-D_{SSD})/D_{ISO}$.

Therefore, the second gantry angle of the radiation source 202 at G1 or G2 can be predetermined according to the following equation:

$$(\alpha_{Tx}) + \{90 - \arcsin(D_{ISO}-D_{SSD})/D_{ISO}\} \quad \text{(IV)}$$

or $$(\alpha_{Tx}) + \{270 + \arcsin(D_{ISO}-D_{SSD})/D_{ISO}\} \quad \text{(V)}$$

where $\alpha_{Tx}$ represents the first gantry angle, $D_{SSD}$ represents a desired value of SSD, and $D_{ISO}$ represents the distance between the isocenter and the radiation source.

Figure 11:
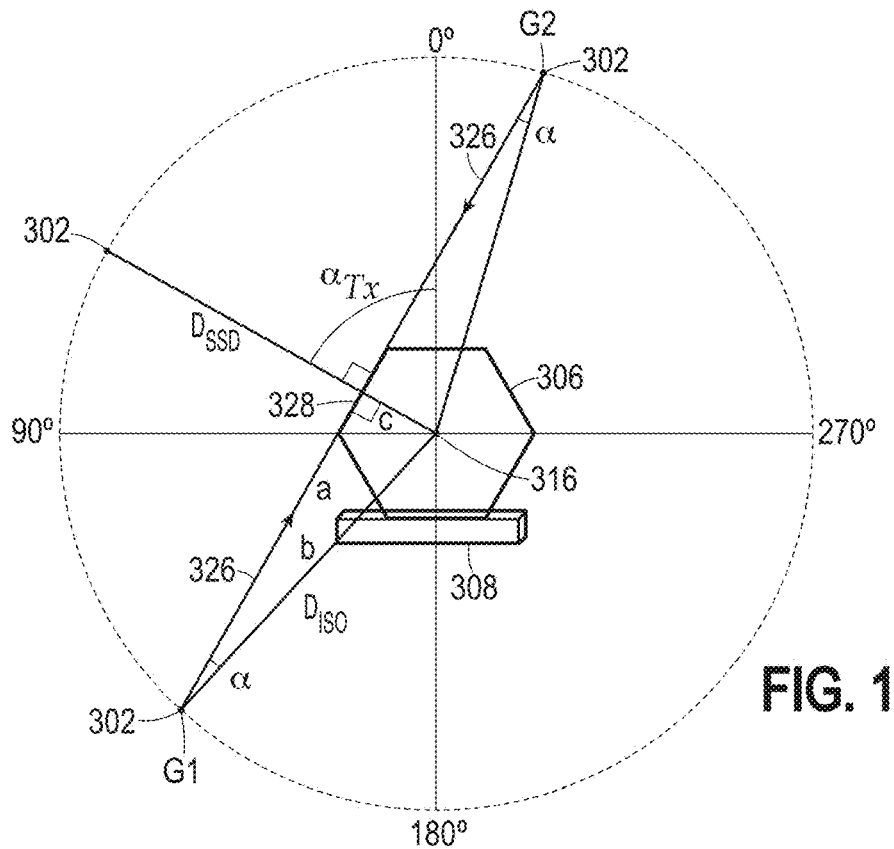
FIG. 11 schematically shows a phantom setup and SSD verification according to further alternative embodiments of the disclosure.

FIG. 11 schematically shows a phantom setup and SSD verification according to a further alternative embodiment of the disclosure. In FIG. 11, a phantom 306 supported by a support 308 is shown to be in a polygonal shape having multiple flat side surfaces. A radiation source 302 positioned at a first gantry angle ($\alpha_{Tx}$) defines a source-to-surface distance ($D_{SSD}$) from the source 302 to a side surface 328 of the phantom 306. The first gantry angle may be an angle for treatment or an angle for various QA measurements. The first gantry angle can be any angle known. According to the disclosure, radiation imaging can be used to set up the phantom 306 and verify if the phantom 306 is positioned at a desired value of SSD.

According to embodiments of the disclosure, the radiation source 302 can be positioned at a predetermined second gantry angle, indicated at G1 or G2, such that a ray of radiation 326 from the source 302 is aligned with an imaginary side surface located at the desired SSD value. If the phantom 306 is setup correctly at the desired value of SSD, the ray of radiation 326 from the source 302 at the second gantry angle G1 or G2 aligns with the side surface 328 of the phantom 306, forming an image showing a sharp or crisp interface between the phantom 306 and the surrounding medium because the resulting penumbra is minimal. On the other hand, if the phantom 306 is not set up at the correct SSD, the radiation beam from the source 306 at the second gantry angle will not align with the side surface 328 of the phantom 306. As a result, the portion of the image formed showing the interface of the phantom 306 and the surrounding medium will be blurry due to the large penumbra caused by the scattering effect of radiation passing through the phantom 306.

Similar to the embodiment shown in FIG. 10, the second gantry angle of the source 302 at G1 or G2 can be predetermined according to the following equation:

$$(\alpha_{Tx})+\{90-\arcsin(D_{ISO}-D_{SSD})/D_{ISO}\} \quad \text{(IV)}$$

or $$(\alpha_{Tx})+\{270+\arcsin(D_{ISO}-D_{SSD})/D_{ISO}\} \quad \text{(V)}$$

where $\alpha_{Tx}$ represents the first gantry angle, $D_{SSD}$ represents a desired value of SSD, and $D_{ISO}$ represents the distance between the isocenter and the radiation source.

FIGS. 10 and 11 show that embodiments of the method of the disclosure can be advantageously used to set up phantoms having various shapes or configurations. Verification of source-to-surface distance can be performed for phantoms comprising either a flat and/or a curve surface, positioned either horizontally or non-horizontally.

Various embodiments of a method for phantom setup and verification of SSD have been described in conjunction with FIGS. 1-11. It will be appreciated that more or fewer steps, actions, or processes may be incorporated into the method without departing from the scope of the disclosure. No particular order is implied by the arrangement of blocks shown and described herein unless it is clearly indicated otherwise. It further will be appreciated that the method described in conjunction with FIGS. 1-11 may be embodied in machine-executable instructions (e.g. software). The instructions can be used to cause a general-purpose or special-purpose processor that is programmed with the instructions to perform the operations described. Alternatively, the operations might be performed by specific hardware components that contain hardwired logic for performing the operations, or by any combination of programmed computer components and custom hardware components. The methods may be provided as a computer program product that may include a machine-readable medium having stored thereon instructions that may be used to program a computer (or other electronic devices) to perform the methods. For the purposes of this specification, the term "machine-readable medium" shall be taken to include any medium that is capable of storing or encoding a sequence of instructions for execution by the machine and that causes the machine to perform any one of the methodologies of the present invention. The term "machine-readable medium" shall accordingly be taken to include, but not be limited to, solid-state memories, optical and magnetic disks. Furthermore, it is common in the art to speak of software, in one form or another (e.g., program, procedure, process, application, module, logic, etc.), as taking an action or causing a result. Such expressions are merely a shorthand way of saying that execution of the software by a computer causes the processor of the computer to perform an action or produce a result.

Those skilled in the art will appreciate that various other modifications may be made within the spirit and scope of the invention. All these or other variations and modifications are contemplated by the inventors and within the scope of the invention.

What is claimed is:

1. A method, comprising:
positioning a phantom on a support relative to a radiation source such that a surface of the phantom is horizontally leveled, the radiation source being supported by a gantry rotatable about an isocenter;
positioning the radiation source at a gantry angle predetermined at least based on a desired value of SSD, wherein the positioning of the radiation source at the gantry angle allows a ray of radiation from the radiation source to align with a horizontal surface located at the desired value of SSD;
acquiring an image showing at least a portion of the surface of the phantom using the radiation from the radiation source at the predetermined gantry angle;
verifying, based on an analysis of the image, if the surface of the phantom is positioned at the desired value of SSD.

2. The method of claim 1, wherein the gantry angle is predetermined according to the following Equation (I) or (II):

$$90-\arcsin(D_{ISO}-D_{SSD})/D_{ISO} \quad \text{(I)}$$

or $$270+\arcsin(D_{ISO}-D_{SSD})/D_{ISO} \quad \text{(II)}$$

wherein $D_{SSD}$ represents the desired value of SSD, and $D_{ISO}$ represents a distance from the radiation source to the isocenter.

3. The method of claim 1, wherein the analysis of the image comprises viewing a contrast of at least a portion of the image showing an interface between the phantom and a surrounding medium.

4. The method of claim 3, wherein the analysis of the image comprises measuring a location of the interface between the phantom and the surrounding medium, and comparing the measured location with a value (L) determined by the following Equation (III):

$$L=(D_{ISO}-D_{SSD})/\text{Square root of } 1-[(D_{ISO}-D_{SSD})/D_{ISO}]^2 \quad \text{(III)}$$

wherein $D_{SSD}$ represents the desired value of SSD, and $D_{ISO}$ represents a distance from the radiation source to the isocenter.

5. The method of claim 1, wherein if the verifying confirms that the surface of the phantom is not positioned at the desired value of SSD, the method further comprising adjusting a position of the phantom, and repeating the steps of acquiring an image and verifying based on an analysis of the image.

6. The method of claim 5, wherein the adjusting and repeating are controlled at a console located remotely from the phantom.

7. The method of claim 6, wherein the adjusting of a position of the phantom comprises vertically moving the support.

8. The method of claim 6, wherein the phantom comprises a water phantom and the adjusting of a position of the phantom comprises increasing or decreasing an amount of water in the water phantom.

9. A method, comprising:
positioning an object on a support relative to a radiation source at a first gantry angle such that a source-to-surface distance (SSD) is defined between the radiation source at the first gantry angle and a point on a surface of the object, the radiation source being supported by a rotating gantry;
positioning the radiation source at a second gantry angle predetermined at least based on a desired value of SSD, wherein the positioning of the radiation source at the second gantry angle allows a ray of radiation from the radiation source to align with a surface or be tangent to a point on a surface located at the desired value of SSD;
acquiring an image showing at least a portion of the surface of the object using the radiation from the radiation source at the second gantry angle;
verifying, based on an analysis of the acquired image, if the point on the surface of the object is positioned at the desired value of SSD.

10. The method of claim 9, wherein the second gantry angle is predetermined according to the following Equation (IV) or (V):

$$(\alpha_{Tx})+\{90-\arcsin(D_{ISO}-D_{SSD})/D_{ISO}\} \qquad (IV)$$

or $$(\alpha_{Tx})+\{270+\arcsin(D_{ISO}-D_{SSD})/D_{ISO}\} \qquad (V)$$

where $\alpha_{Tx}$ represents the first gantry angle, $D_{SSD}$ represents a desired value of SSD, and $D_{ISO}$ represents the distance between the isocenter and the radiation source.

11. The method of claim 9, wherein the first gantry angle comprises a non-zero degree.

12. The method of claim 9, wherein the surface of the object comprises a flat surface, and the positioning of the radiation source at the second gantry angle allows a ray of radiation from the radiation source to align with an imaginary flat surface located at the desired value of SSD.

13. The method of claim 9, wherein the surface of the object comprises a curve surface, and the positioning of the radiation source at the second gantry angle allows a ray of radiation from the radiation source to be tangent to an imaginary point on an imaginary curve surface located at the desired value of SSD.

14. The method of claim 9, wherein the analysis of the image comprises viewing a contrast of at least a portion of the image showing an interface between the object and a surrounding medium.

15. The method of claim 9, wherein if the verifying confirms that the point on the surface of the object is not positioned at the desired value of SSD, the method further comprises adjusting a position of the object, and repeating the steps of acquiring an image and verifying based on an analysis of the image.

16. A method, comprising:
positioning a radiation source at a known location, wherein the positioning of the radiation source at the known location allows a ray of radiation from the radiation source to align with a surface or be tangent to a point on a surface located at a desired value of SSD;
positioning an object on a support such that a point on a surface of the object is located at or approximate to the desired value of SSD;
acquiring an image showing at least a portion of the surface of the object using the radiation from the radiation source at the known location;
verifying, based on an analysis of the image, if the point on the surface of the object is positioned at the desired value of SSD.

17. The method of claim 16, wherein the analysis of the image comprises analyzing a penumbra on at least a portion of the image showing an interface between the object and a surrounding medium.

18. The method of claim 16, wherein if the verifying confirms that the surface or the point on the surface of the object is not positioned at the desired value of SSD, the method further comprises adjusting a position of the object, and repeating the steps of acquiring an image and verifying based on an analysis of the image.

19. The method of claim 16, wherein the surface of the object comprises a flat surface, and the positioning of the radiation source at the known location allows a ray of radiation from the radiation source to align with a flat surface located at the desired value of SSD.

20. The method of claim 16, wherein the surface of the object comprises a curve surface, and the positioning of the radiation source at the known location allows a ray of radiation from the radiation source to be tangent to a point on a curve surface located at the desired value of SSD.

* * * * *

UNITED STATES PATENT AND TRADEMARK OFFICE
CERTIFICATE OF CORRECTION

PATENT NO. : 10,898,158 B2
APPLICATION NO. : 16/300923
DATED : January 26, 2021
INVENTOR(S) : Constantin et al.

Page 1 of 1

It is certified that error appears in the above-identified patent and that said Letters Patent is hereby corrected as shown below:

In the Specification

At Column 6 Line 48, replace "QAtasks" with - QA tasks -.

At Column 8 Line 49, replace "side cis" with - side c is -.

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*